United States Patent [19]

Drew et al.

[11] 4,413,507
[45] Nov. 8, 1983

[54] METHOD AND ARRANGEMENT FOR DETERMINING TOOL WEAR

[75] Inventors: Jeffrey-Michael Drew; Max-Gerhard Seitz, both of Munich; Hans-Peter Kehrer, Unterhaching; Gottfried Eichelbroenner, Berlin, all of Fed. Rep. of Germany

[73] Assignee: Siemens Aktiengesellschaft, Berlin & Munich, Fed. Rep. of Germany

[21] Appl. No.: 291,093

[22] Filed: Aug. 7, 1981

[30] Foreign Application Priority Data

Aug. 7, 1980 [DE] Fed. Rep. of Germany ....... 3029957

[51] Int. Cl.³ .............................................. G10N 19/00
[52] U.S. Cl. ........................................ 73/104; 73/587; 73/659
[58] Field of Search .................. 73/104, 658, 659, 801, 73/587

[56] References Cited

U.S. PATENT DOCUMENTS

| 3,148,537 | 9/1964 | Berwin et al. | 75/658 |
| 3,713,127 | 1/1973 | Keledy et al. | 73/587 |
| 3,793,627 | 2/1974 | Darrel et al. | 73/104 X |
| 4,007,630 | 2/1977 | Noda | 73/659 |
| 4,220,995 | 9/1980 | Shoda | 73/104 X |
| 4,332,161 | 1/1982 | Kakino | 73/104 |

FOREIGN PATENT DOCUMENTS

| 55-72809 | 6/1980 | Japan | 73/587 |
| 55-72810 | 6/1980 | Japan | 73/587 |
| 56-76362 | 6/1981 | Japan | 73/587 |
| 56-76363 | 6/1981 | Japan | 73/587 |
| 456167 | 2/1975 | U.S.S.R. | 73/658 |
| 665220 | 5/1979 | U.S.S.R. | 73/658 |

*Primary Examiner*—S. Clement Swisher
*Attorney, Agent, or Firm*—Hill, Van Santen, Steadman & Simpson

[57] ABSTRACT

In a method and apparatus for monitoring tool wear, noise emission signals associated with a cutting operation of the tool are monitored and evaluated to determine when the tool has become blunt. With the system disclosed, friction noises associated with the cutting tool are excluded from analysis.

7 Claims, 6 Drawing Figures

~500 μm

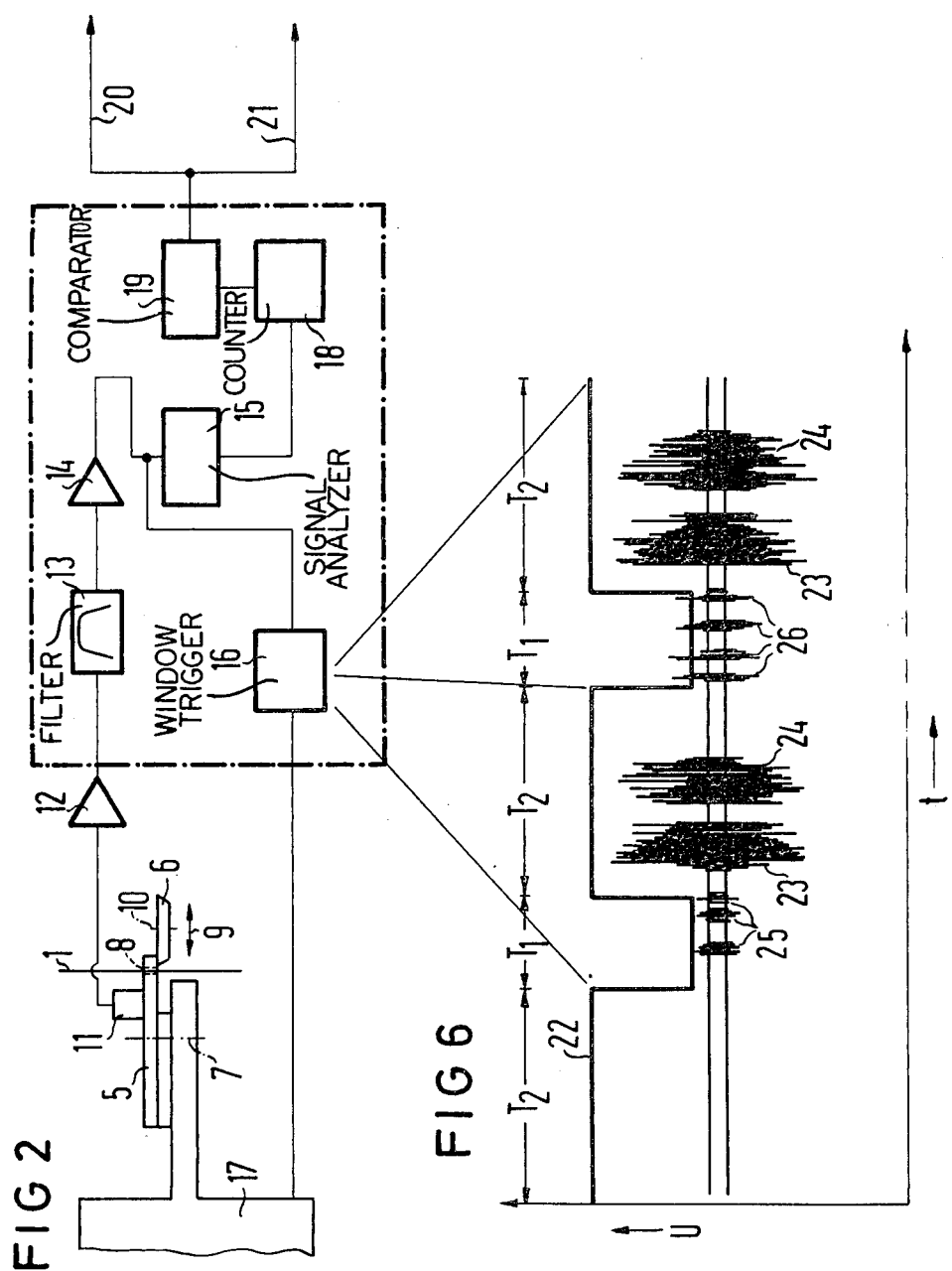

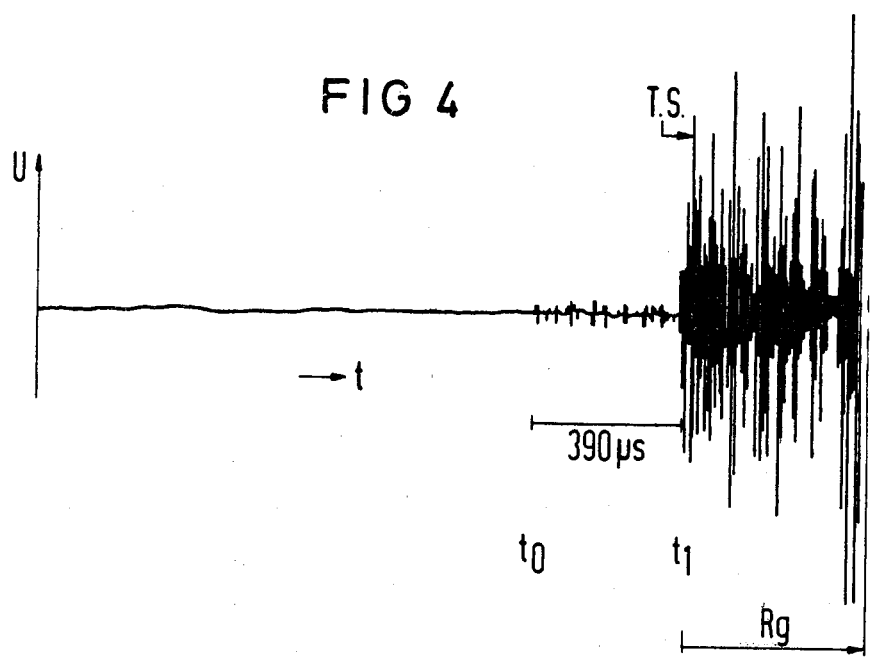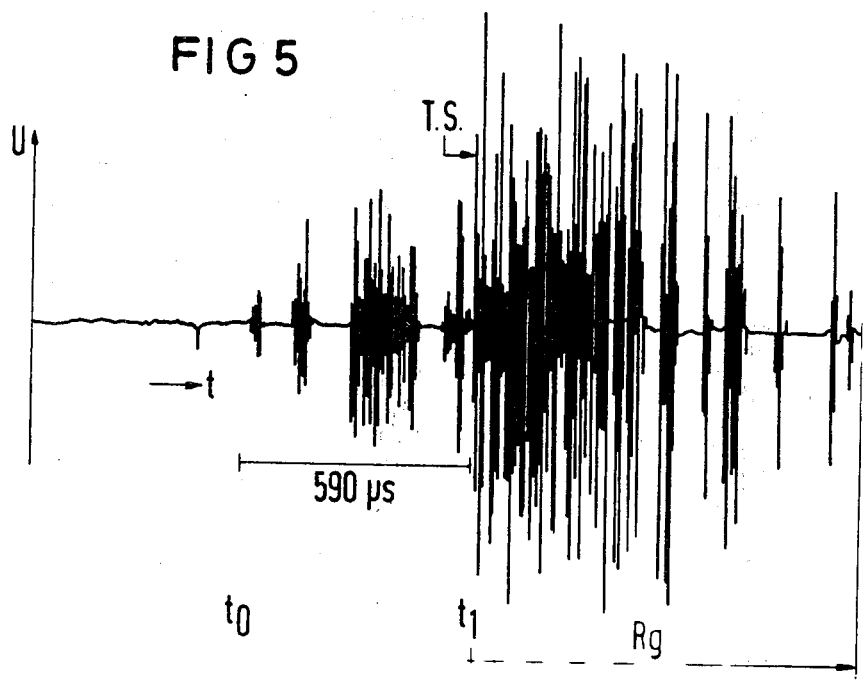

METHOD AND ARRANGEMENT FOR DETERMINING TOOL WEAR

BACKGROUND OF THE INVENTION

The invention relates to a method for determining tool wear, particularly in the cutting of tungsten wires, as well as an arrangement for the implementation of said method.

Tungsten wires are employed, for example, as coils in the manufacture of incandescent lamps. Since tungsten wire coils are usually manufactured in wound form in a continuing sequence on a core, they must be cut into lengths with a specific dimension in accordance with its intended use. In the case of coils that are wound with a break, the separation occurs in the center of the break. Accordingly, the cutting into sections usually ensues with the assistance of a fixed injector knife and a blade knife which is moved back and forth at right angles with respect to the coil. During the cutting of the incandescent lamp coils, as the cutting tools increasingly wear, a more or less strong formation of hooks occurs at the coil. Such hooks lead to the mutual entanglement of the coils and then disrupt the automatic sequence in the lamp manufacture and, moreover, lead to rejects which lie in the magnitude of 2% of the manufacturing quota. Accordingly, a particular problem arises, since the tool wear producing the formation of hooks cannot be predicted as a result of being subject to very great fluctuation. Experience has shown that the actual number of cuts, i.e., the plurality of cuts which can be carried out without re-grinding the tools, lies between 10,000 and 30,000 cuts. This fluctuation in the number of cuts can be attributed, among other things, to differences in the tenacity of the tungsten wire. Thus, the tools must be constantly monitored, which was previously carried out in such a manner that random samples of the cut coils were checked under a magnifying glass for the formation of hooklets every five to ten minutes. This monitoring operation is very personnel-intensive and requires very reliable personnel.

SUMMARY OF THE INVENTION

An object of the invention is to provide a method and a device in order to be able to automatically determine the tool wear early enough such that the rejects can be kept as small as possible and no disruptions in the manufacturing sequence can occur.

This object is achieved by means of the inventive method in that the noise emission signals of the cutting operation are monitored and evaluated.

The fact is utilized that noise is emitted in the plastic deformation or formation of fractures in many metallic materials. However, the difficulty lies in that intense friction noises between the cutting tool and the injector knife occur both during cutting with blunt, as well as during cutting with sharp cutting tools. This problem is solved by blanking out the noise emission signals of the cutting operation and monitoring with the assistance of an internal trigger signal. This monitoring window can be determined, for example, by means of analysis of the noise emission signals. Thus, it has been shown that approximately 500 μs before the beginning of the friction sounds, noise emission signals of the cutting operation occur which can be separated or blanked out and evaluated with the assistance of a trigger window.

An arrangement for implementing the inventive method comprises coupling a sound pickup to the cutting tool or to the injector knife, the output signals of the sound pickup being supplied via a window trigger to a signal analyzer for evaluation. It has turned out that the injector knife functions as an ideal waveguide so that the sound pickup can be coupled directly to the injector knife. Preferably, the amplitudes of the blanked or separated out cutting signals are monitored with the assistance of a comparator and a warning signal is emitted when a prescribed value is exceeded.

BRIEF DESCRIPTION OF THE DRAWINGS

FIG. 2 is a block diagram of an arrangement for implementing a method of the invention;

FIG. 4 is a graphic illustration of the noise emission signals of the cutting and friction noises given a cut with sharp cutting tools;

FIG. 5 is a graphic illustration of the noise emission signals of the cutting and friction noises given a cut with blunt cutting tools; and FIG. 6 is a graphic illustration of the noise emission signals given an arrangement according to FIG. 2.

DESCRIPTION OF THE PREFERRED EMBODIMENTS

Figure 1:
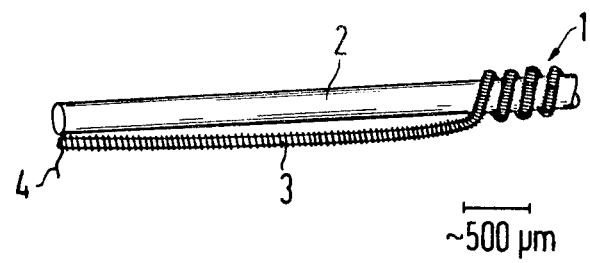
FIG. 1 illustrates a portion of a cut-off coil with hooklets.

FIG. 1 shows an incandescent lamp coil 1 which, for reasons of fabrication, is wound around a metallic core 2. The front part 3 of the coil is illustrated as a part of an interruption, whereby a hooklet 4 which is caused by blunt cutting tools is formed at the front end. These hooklets 4 are very disruptive because they can hook into other coils. In order to be able to perceive this hooklet formation at an early point in time, a sample embodiment of an arrangement for identifying the noise emission signals is illustrated in FIG. 2.

In FIG. 2, 1 again indicates an incandescent lamp coil which is to be cut into appropriate pieces with the assistance of an injector knife 5 and a cutting tool 6. The injector knife 5 is designed disk-like and exhibits bores 8 with sharp cutting edges at its circumference concentric with respect to its axis 7. The bores 8 are adapted to the diameter of the coils 1. The injector knife 5 can be adjusted around the axis 7 in order to bring the next bore 8 into play in case the cutting edge at the edge of the bore has become blunt.

The cutting tool 6 is likewise designed as a disk and can be moved back and forth in the direction of arrow 9, whereby the cutting edge of the cutting tool 6 is set lightly against the injector knife 5 in order to obtain a smooth cut. As soon as the cutting edge of the cutting tool 6 has become blunt, rotation of the cutting tool 6 around a shaft 10 by a specific angle can bring a new area of the cutting tool 6 into play.

A sound pickup 11 is coupled to the injector knife 5, said sound pickup picking up the noise emission signals and supplying them via a preamplifier 12, a filter 13 and a main amplifier 14 to a signal analyzer 15 which records the noise emission signals. With the assistance of a window trigger 16, the area in which only cutting noises occur is blanked or separated out of the noise emission signals. The window trigger 16 receives its signal via a line which is connected to a portion 17 of the cutting device in order to indicate that, in the sample embodiment which has been selected, the trigger signal is triggered externally, i.e., as a function of the motion of the cutting tool 6. The window trigger 16, however, can also be triggered by means of an internal signal, for example, as a function of the beginning of the friction noises as shall be explained in greater detail on the basis of FIGS. 4 and 5. The signal analyzer 15 is connected via a counter 18 to a comparator 19 which, for example, compares the amplitude and/or normal duration of the noise emission signals to a value which is still tolerable. Signals which indicate whether the tool is still good or has already become too worn can be emitted via outputs 20 and 21.

Figure 3:
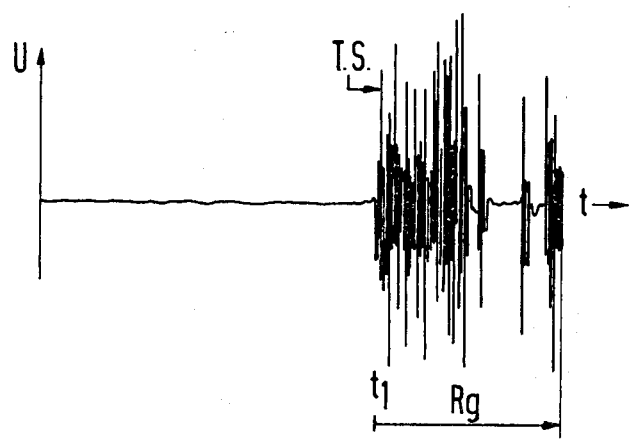
FIG. 3 is a graphic illustration of noise emission signals of friction noises in a cutting operation without a coil.

FIG. 3 shows the amplitudes as a function of time of the noise emission signals which arise given a relative motion between the injector knife and the cutting tool without a coil being cut. Friction noises occur beginning at point in time $t_1$, as indicated by means of an arrow Rg.

FIG. 4 shows a graphic illustration of the noise emission signals as a function of the time when a coil is being cut. As can be seen from FIG. 4, cutting noises occur 390 $\mu$s before the occurrence of the friction noises Rg. These cutting noises, however, are so slight that practically no hooklet formation can occur.

In contrast thereto, FIG. 5 shows a graphic illustration of the noise emission signals, whereby cutting noises already occur 590 $\mu$s before point in time $t_1$, said cutting noises exhibiting an amplitude such that one can suspect that the cutting tool has become blunt. The range $t_0$ through $t_1$ thus can be employed for monitoring the cutting operation. This range can be identified, for example, with the assistance of a trigger signal T.S. which indicates the occurrence of the friction noises between the injector knife and the cutting tool.

FIG. 6 shows a graphic illustration of the noise emission signals as they occur in the cutting operation. 22 indicates the threshold voltage of the window trigger 16. 23 and 24 indicate the friction noises between the cutting tool 6 and the injector knife 5, and 25 and 26 indicate cutting noises. The areas $T_1$ are blanked out with the assistance of the window trigger 16 and are supplied to the signal analyzer 15 in which calculations are to be carried out with the occurrence of the pure cutting noises. There, the friction noises 23 of the forward motion and the friction noises 24 of the return motion of the cutting tool 6 are allocated. The cutting noises 25 lie before the friction noises 23 but, in the selected sample embodiment, they lie below the threshold of the trigger 16.

In contrast thereto, the noise emission signals 26 are of a magnitude that they exceed the threshold of the trigger 16. In this case, thus a signal is placed on the line 21 which indicates that the cutting tool has become blunt to an inadmissible degree. In this case, one must see to it that the cutting tool is adjusted or replaced and, if need be, must be re-ground.

Specific circuitry has not been shown for the filter 13, signal analyzer 15, window trigger 16, and comparator 19, since such devices are well known to those skilled in this art. For example, the filter 13 is a band-pass filter which permits frequencies corresponding to the cutting noises to pass therethrough to the exclusion of other signals associated with unwanted noises. The window trigger 16 can utilize a micro-switch to sense the position of the injector knife 5 so as to selectively connect through with a switching device signals from the main amp 14 to the signal analyzer 15. Alternatively, the high amplitude friction noises 23 could be employed to trigger a switching device into an off mode and then permitting the switching device to assume the on or pass-through mode after a predetermined delay determined by a delay member. The signal analyzer 15 can comprise circuitry for creating voltage pulses of equal height corresponding to individual noise pulses associated with the cutting noises 25. Such individual output pulses of given height would then be counted in the counter 18 and compared to an overall maximum value of the comparator 19. Alternatively, the signal analyzer may integrate the cutting noises to create an output voltage which is then compared to a threshold value in the comparator 19. Alternatively, the average amplitude of the cutting noise signals 25 can be determined in an averaging circuit whose output is then fed to the comparator 19 for comparison with the predetermined threshold value.

In an alternate form of the invention, the signal analyzer 15 may be a frequency measuring device such as a frequency meter or frequency counter. When blunting of the cutting tool causes a change in frequency of the cutting noises, such change in frequency is determined by the comparator 19 which would function as a frequency comparator. When the frequency of the cutting noises change beyond a predetermined maximum range, the comparator would initiate an output signal.

Although the invention has been described with respect to preferred embodiments, it is not to be so limited as changes and modifications can be made which are within the full intended scope of the invention as defined by the appended claims.

We claim as our invention:

1. A tool wear monitoring device for monitoring wear of a cutting tool, comprising:
   a sound pick-up means coupled to the cutting tool for creating output signals responsive to cutting noises associated with the cutting tool during operation;
   window trigger means connected to control the output signals for excluding friction noises associated with the cutting tool while permitting the cutting noises to pass through;
   signal analyzer means connected to receive the output signals as controlled by the window trigger means for evaluating a magnitude of the cutting noises in comparison to a predetermined threshold level beyond which the cutting tool is considered to be blunt; and
   the window trigger means selecting the cutting noises for passage therethrough by sensing a physical movement of at least a portion of the cutting tool.

2. A device according to claim 1 wherein the cutting tool is comprised of a cutting disc and an injector knife which cooperates therewith, the window trigger means sensing movement of the injector knife.

3. A device according to claim 1 wherein the sound pick-up is mounted on an injector knife portion of the tool which has a bore means therein for receiving a wire, and wherein a cutting member is provided which cooperates with cutting edges of the bore for shearing of the wire.

4. The device of claim 1 wherein the signal analyzer means comprises a signal analyzer connecting to a counter which in turn connects to a comparator.

5. A tool wear monitoring device for monitoring wear of a cutting tool, comprising:

a sound pick-up means coupled to the cutting tool for creating output signals responsive to cutting noises associated with the cutting tool during operation;

window trigger means connected to control the output signals for excluding friction noises associated with the cutting tool while permitting the cutting noises to pass through;

signal analyzer means connected to receive the output signals as controlled by the window trigger means for evaluating a magnitude of the cutting noises in comparison to a predetermined threshold level beyond which the cutting tool is considered to be blunt; and the window trigger means sensing for either the cutting noises or the friction noises and comparing these noises relative to a predetermined amplitude in order to exclude the friction noises.

6. A device according to claim 5 wherein the window trigger means senses for a beginning of the friction noises.

7. A device according to claim 6 wherein after sensing the beginning of the friction noises a time delay means is triggered.

* * * * *